United States Patent [19]

Hughes et al.

[11] Patent Number: 5,316,768
[45] Date of Patent: May 31, 1994

[54] PHARMACEUTICAL COMPOSITIONS HAVING ANTIVIRAL ACTIVITY AGAINST HUMAN CYTOMEGALOVIRUS

[75] Inventors: Bronwyn G. Hughes; Steven G. Wood, both of Orem, Utah

[73] Assignee: Murdock International Corporation, Springville, Utah

[21] Appl. No.: 943,748

[22] Filed: Sep. 11, 1992

Related U.S. Application Data

[62] Division of Ser. No. 635,361, Dec. 28, 1990, abandoned.

[51] Int. Cl.$^5$ ............................................. A61K 35/78
[52] U.S. Cl. ..................................... 424/433; 424/43; 424/195.1; 424/427; 424/430; 424/436; 424/464
[58] Field of Search .................... 424/195.1, 433, 427, 424/430, 436, 464

[56] References Cited

U.S. PATENT DOCUMENTS

| | | | |
|---|---|---|---|
| 4,670,265 | 6/1987 | Sydiskis et al. | 424/195.1 |
| 4,851,224 | 7/1989 | McAnalley | 424/195.1 |
| 4,898,891 | 2/1990 | Lavie et al. | 514/732 |
| 5,118,673 | 6/1992 | Carpenter et al. | 514/935 |
| 5,149,718 | 9/1992 | Meruelo et al. | 514/732 |

FOREIGN PATENT DOCUMENTS

| | | |
|---|---|---|
| 0256452 | 2/1988 | European Pat. Off. |
| 59-190921 | 10/1984 | Japan |
| 121215 | 5/1989 | Japan |

OTHER PUBLICATIONS

Adler, Stuart P., M.D., "Cytomegalovirus and Child Day Care: Evidence for an Increased Infection Rate among Day-Care Workers", *The New England Journal of Medicine*, vol. 321, No. 19, pp. 1290-1296, (Nov. 1989).

Borissenko, S. et al., "Obtaining a High Percentage of Explants with Negative Serological Reactions against Viruses by Combining Potato Meristem Culture with Antiphytoviral Chemotherapy," *Phytopathologische Zeitschrift*, vol. 114, pp. 185-188 (1985).

Burns, Noah J. III, et al., "A newly developed immunofluorescent assay for determining the Pichinde virus-inhibitory effects of selected nucleoside analogues," *Antiviral Research*, vol. 10, pp. 89-98 (1988).

Cecil, "Fever and Febrile Syndromes" *Essentials of Medicine*, 1990.

Griffiths, P. D., et al., "The status of CMV as a human pathogen," *Epidemiology and Infection*, vol. 100, pp. 1-(1988).

Harnden, M. R., et al., "Screening leads-natural products," *Approaches to Antiviral Agents*, Chapter 6, pp. 153-180 (1985).

(List continued on next page.)

*Primary Examiner*—Paul R. Michl
*Assistant Examiner*—James M. Spear
*Attorney, Agent, or Firm*—Workman, Nydegger & Jensen

[57] ABSTRACT

The present invention is directed to the use of antiviral compounds having the following generalized structure:

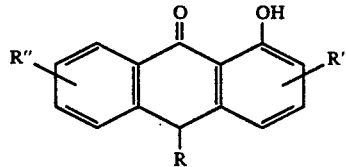

wherein R is 2H or =O; R' is OH, H, or COOH (single substitution); and R" is OH, H, or alkyl; and pharmaceutically acceptable salts thereof as therapeutic substances having antiviral activity against human cytomegalovirus ("HCMV") and for treating diseases caused by HCMV. Dimeric forms of the forgoing antiviral compounds having antiviral activity against HCMV are also disclosed. Pharmaceutical compositions containing the disclosed antiviral compounds are disclosed for topical and systemic administration.

6 Claims, 4 Drawing Sheets

OTHER PUBLICATIONS review," *The Linnean Society of London*, pp. 157–177 (1985).

Robins, Roland K., et al., "Design of Nucleoside Analogs as Potential Antiviral Agents," *NATO Advanced Study Institute on Antiviral Drug Development: a Multidisciplinary Approach* vol. 143, pp. 11–54 (1987).

Sato et al., "Inhibitors of sialidase as microdicides," *Chemical Abstracts*, vol. 112, p. 448 (1990).

Schinazi et al., "Anthraquinones as a new class of antiviral agents against human immunodeficiency virus," *Antiviral Research*, vol. 13, pp. 265–272 (1990).

Schuster, Von Gottfried, et al., "In-vivi-und in-vitro Inaktivierung des Tabakmosaikvirus durch Extrake aus Physarum nudum Macbr. und Hypericum perforatum L." *Inst. F. Tabakforschung*, vol. 26, pp. 28–35 (1979).

Serkedjieve, J., et al., "Antiviral Activity of the Infusion (SHS-174) from Flowers of Sambucus nigra L., Aerial Parts of Hypericum perforatum L., and Roots of Saponaria officinalis L. Against Influenza and Herpes Simplex Viruses," *Phytotherapy Research*, vol. 4, No. 3, pp. 97–100 (1990).

Suga, T., et al., "The Efficacy of the Aloe Plants Chemical Constituents and Biological Activities" *Cosmetics & Toiletries*, vol. 98 (Jun. 1983).

Suzutani, Tatsuo, et al., "Effects of Various Nucleosides on Antiviral Activity and Metabolism of 1-β-D-Arabinofuranosyl-E-5-(2-Bromovinyl) Uracil against Herpes Simplex Virus Types 1 and 2," *Antimicrobial Agents and Chemotherapy*, vol. 32, No. 10, pp. 1547–1551 (Oct. 1988).

Suzutani, Tatsuo, et al., "Efficacies of Antiherpesvirus Nucleosides Against Two Strains of Herpes Simplex Virus Type 1 in Vero and Human Embryo Lung Fibroblast Cells," *Antimicrobial Agents and Chemotherapy*, vol. 32, No. 7, pp. 1046–1052 (Jul. 1988).

Sydiskis, R. J., et al., "Inactivation of Herpes Simplex Virus by Anthraquinones Isolated From Plants," *J. Dent. Res.*, vol. 68, p. 935 (Jun. 1989).

Wetzler, Christine et al., "Zur Kennzeichnung der antiphytoviralen Wirkung von Extrakten aus Physarum nudum Macbr. und Hypericum perforatum L. gegenüber dem Tabakmosaik-Virus (tobacco mosaci virus, Hirsch, Martin S., et al., "Antiviral Therapy: How can one kill a virus and not the host cell in which it is physically and functionally incorporated? New antiviral drugs exploit the subtle molecular contrasts between virus and host," pp. 76–85 references unknown.

Hoffmann, C. E., "Screening leads-synthetic compounds," *Approaches to Antiviral Agents*, Chapter 5, pp. 135–151 (1985).

Inoue, Takami, et al., "In Vitro Bone Marrow Toxicity of Nucleoside Analogs against Human Immunodeficiency Virus," *Antimicrobial Agents and Chemotherapy*, vol. 33, No. 4, pp. 576–579 (Apr. 1989).

Ivan, Halm, "Elözetes Vizsgálatok a Hypericum perforatum herpesterápiában való felhasználására," *Gyo gyszereszet* vol. 23, pp. 217–218, 1979.

Konoshima et al., "Studies on inhibitors of skin tumor promotion," *Journal of Natural Products*, vol. 52, No. 5, pp. 987–995 (Sep.–Oct. 1989).

Lavie, Gad et al., "Studies of the mechanisms of action of the antiretroviral agents hypericin and pseudohypericin," *Proc. Natl. Acad. Sci. USA*, vol. 86, pp. 5963–5967 (Aug. 1989).

Meruelo, Daniel, et al., "Therapeutic agents with dramatic antiretroviral activity and little toxicity at effective doses: Aromatic polycyclic diones hypericin and pseudohypericin," *Proc. Natl. Acad. Sci., USA*, vol. 85 (Jul. 1988).

Minshi, Zheng, "An Experimental Study of the Anti--HSV-II Action of 500 Herbal Drugs," *Journal of Traditional Chinese Medicine*, vol. 9, No. 2, pp. 113–116 (1989).

Reynolds, T., "The compounds in Aloë leaf exudates: a TMV)," *Arch. Phytopathol. u. Pflanzenschutz*, vol. 17, No. 5, pp. 333–340 (1981).

Yarchoan, Robert, et al., "Progress in the Development of Antiviral Therapy for HTLV-III-Associated Diseases," *Important Advances in Oncology*, Chapter 15, pp. 293–311 (1987).

"Hypericum Tannins or Influeria Virus," *Mikrobiologichnyi Zhurnal*, vol. 34, No. 6, pp. 768–771 (1971).

"International Conference on Aids," *Quebec 1989 (5th), pp. 544, 561, 642, 659, 662.*

"Products: AIDS-new approaches to drug design," *SCRIP*, No. 1456, p. 26 (Oct. 1989).

EMODIN

EMODIN ANTHRONE

EMODIN BIANTHRONE

PROTOHYPERICIN

HYPERICIN

RHEIN

ALIZARIN

QUINALIZARIN

QUINIZARIN 1,8-DIHYDROXYANTHRAQUINONE

PHYSCIONE

ALOE-EMODIN

ALOIN

CHRYSOPHANOL

ANTHRAFLAVIC ACID

ANTHRARUFIN

PURPURIN

ANTHRAQUINONE

SENNOSIDE A & B

Antiviral Activity of Emodin Bianthrone or DHPG at Various Times of Exposure to HCMV-Infected MRC-5 Cells

PHARMACEUTICAL COMPOSITIONS HAVING ANTIVIRAL ACTIVITY AGAINST HUMAN CYTOMEGALOVIRUS

This application is a divisional of application Ser. No. 635,361, filed Dec. 28, 1990 now abandoned.

BACKGROUND

1. Field of the Invention

The present invention is directed to compositions having antiviral activity against the human cytomegalovirus ("HCMV"). More particularly, the present invention concerns pharmaceutical compositions containing the disclosed antiviral compounds which may be administered both topically and systemically.

2. Technology Review

Viruses are submicroscopic infective agents that are composed of either an RNA or a DNA core of genetic material encased in a protein shell. They are often further wrapped in lipid-containing envelopes, but they do not have a semipermeable membrane. Viruses multiply only within living cells; they commandeer the host cell to synthesize viral proteins and viral nucleic acids which are subsequently incorporated by final assembly into new virion particles.

There are various types of viral infections which may vary in severity from mild and transitory infections to illnesses that terminate in death. In lytic infections the virus replicates by inducing the cell to copy the viral genetic material and form additional virus particles. The infected cell is then lysed, releasing the virion particles. Lytic infections often spread rapidly throughout the population of vulnerable cells. The common cold and polio are examples of lytic infections.

In persistent infections, the virus does not always kill the infected cell. New virus particles are often released gradually; the cell survives intact and continues to divide, although its metabolism may undergo change. Persistent infections may also be characterized by a low level lytic infection involving only a small percentage of cells. In either case, a persistent infection may continue for months or years without causing overt disease. Hepatitis B virus, human leukemia viruses, and human immunodeficiency virus ("HIV") which is the cause of acquired immune deficiency syndrome ("AIDS"), are examples of viruses causing persistent infections.

Finally, in latent infections the genetic material of the virus can become integrated into the host cell's chromosomes which are reproduced during cell division and transmitted to the daughter cells. Under certain conditions latent viruses can be reactivated, thereby resulting in an active infection. Herpes viruses are characterized by periods of latency alternating with periods of active viral replication.

Human cytomegalovirus ("HCMV") is a member of the DNA herpes virus family. HCMV has been isolated from saliva, urine, breast milk, blood, semen, and vaginal secretions. It can be transmitted in utero, despite the presence of high maternal antibody titers. Once infected, the individual conserves the virus in a latent or persistent form throughout life.

Serological surveys indicate that most adults have been infected with HCMV. Following primary infection, which is almost always asymptomatic in people with normal immunity, the virus establishes latency. The virus is probably maintained in this latent state by immune surveillance mechanisms since immunosuppression frequently leads to reactivation of the virus. Re-infection with, or reactivation of, HCMV can give rise to life-threatening disease.

HCMV infections are manifested in a variety of disease states. Such infections in young children are often expressed as severe respiratory infection, and in older children and adults, they are expressed as anicteric hepatitis and mononucleosis. Infection with HCMV during pregnancy can lead to congenital malformation resulting in mental retardation and deafness.

HCMV pneumonitis is the most common single cause of death following bone marrow transplantation, and disseminated HCMV infection is a major cause of mortality and morbidity in patients with renal allografts or with AIDS. Recent evidence also suggests the possible role of HCMV as an oncogenic cofactor in certain tumors such as cervical carcinoma and Kaposi's sarcoma.

Like other herpes viruses, HCMV has a propensity to reactivate, particularly in immunosuppressed patients. Thus, HCMV infections present a major clinical problem for AIDS patients and other immunocompromised individuals such as organ transplant recipients and other patients receiving immunosuppressive drugs. Among AIDS patients, HCMV is the causative agent of certain invasive diseases such as retinitis, which is sight threatening, peripheral retinitis (an earlier form of the infection), and colitis.

In modern medical practice, HCMV is a significant pathogen whose ultimate control by means of immunization or drug therapy has become an important objective. So far, preliminary vaccination efforts have been unsuccessful, and no ideal therapeutic agent has been developed which can efficiently contain HCMV infection. Vaccination efforts are probably unsuccessful because the virus can infect one cell from another without being exposed to the cell milieu in which the vaccine-stimulated antibodies act. Prophylaxis and therapy using HCMV immune globulins have met with only moderate success. In addition, therapeutic agents developed for treating HCMV infections have the common disadvantages of some type of toxicity to the host and the inability to rid the host of latent infection.

A major obstacle in developing suitable drugs possessing antiviral activity against HCMV is the ability to distinguish between the virus and the patient's own cells. HCMV, like other viruses, can only replicate by physically invading a cell and using the cell's biochemical pathways to make new viral proteins and genetic material.

Because virus replication cycles are intimately connected with the functions of the host cell, there are few features peculiar to the virus that are not also present in the host. This makes selective attack on the virus difficult. Therefore, antiviral compounds generally represent a compromise between suppression of virus replication while minimizing adverse effects on the host.

Nucleoside analogs represent a major class of compounds which exhibit significant antiviral activity. These compounds are related to the naturally occurring precursors of DNA or RNA. Nucleoside analogs consist of heterocyclic bases linked to sugars or sugar-like groups.

Because nucleosides are necessary for normal DNA and RNA synthesis, certain chemically altered nucleosides interfere with the synthesis and function of DNA and/or RNA. Nucleoside analogs were first synthesized as potential anticancer drugs capable of slowing or blocking the accelerated DNA production of rapidly dividing cancer cells, but later some were found to also possess antiviral activity. Some of these compounds rapidly cross the cellular plasma membrane, thereby gaining rapid entry into the cell. Nevertheless, the cytotoxicity of nucleoside analogs remains a major drawback to their effectiveness and specificity for treating viral infections.

In discussing compositions effective against viruses, it is important to note the distinction between "antiviral" compositions and "virucidal" compositions. This distinction is most clearly understood with reference to the experimental procedures used to determine the activity.

In determining "virucidal" activity, the virus is exposed to the test composition before inoculating the tissue culture. The degree of virucidal activity is measured by comparing the quantity of virus plaques formed in tissue cultures inoculated by chemically treated virus with tissues cultures inoculated by untreated virus.

In determining "antiviral" activity, the tissue culture is inoculated with the virus and incubated for a period of time. The infected tissue culture is then treated with the test composition. The degree of antiviral activity is measured by comparing the quantity of virus plaques present in chemically treated tissue cultures with untreated tissue cultures.

Compositions that have virucidal activity do not necessarily have antiviral activity. Similarly, compositions that have virucidal or antiviral activity against one virus or even a class of viruses, do not necessarily have virucidal or antiviral activity against other viruses, even within the same class. Thus, there is a high degree of unpredictability in both the mode of activity and virus selectivity for virucidal and antiviral compositions.

Compositions having virucidal activity are particularly important as topical disinfectants. In general, virucidal compositions have doubtful usefulness in treating patients already infected with a virus. In contrast, antiviral compositions are primarily used to treat patients having existing viral infections.

Of the known antiviral agents, foscarnet, acyclovir, and ganciclovir (shown below) are presently undergoing clinical evaluation for effectiveness in the treatment of HCMV infections in AIDS patients.

Ganciclovir, a nucleoside derivative also known as "DHPG", has been approved to treat HCMV retinitis in individuals with AIDS based on the positive effects seen in short term clinical trials. Although this represents encouraging progress in the treatment of HCMV infections, ganciclovir is not an ideal chemotherapeutic agent. The drug possesses serious toxic side effects such as neutropenia (an abnormally small number of neutrophil cells in the blood) which will preclude use of ganciclovir in an estimated 40% of all AIDS HCMV patients. Recently, ganciclovir-resistent mutant viral strains have been reported in AIDS patients treated with the drug and have been associated with severe progression of the disease.

From the foregoing, it will be appreciated that what is needed in the art are active pharmaceutical compositions having novel antiviral activity against HCMV and methods of administering said compositions.

In addition, it would be a significant advancement in the art to provide non-nucleoside antiviral compositions and methods of administering said compositions which specifically attack HCMV without substantially inhibiting normal cellular metabolism.

Such antiviral compositions and administration methods are disclosed and claimed herein.

BRIEF SUMMARY AND OBJECTS OF THE INVENTION

The present invention is directed antiviral pharmaceutical compositions containing emodin, related hydroxyanthraquinone derivatives and salts thereof which are effective against human cytomegalovirus ("HCMV") infections. It has been found that emodin and certain other hydroxyanthraquinone derivatives have significant antiviral activity against HCMV.

Emodin and other related hydroxyanthraquinone derivatives are not nucleoside analogs. Therefore, it is reasonable to presume that these compounds would not possess the same mechanism of action and adverse side effects associated with nucleosides. In addition, emodin is naturally occurring and has safely been used as a cathartic. Pharmaceutical compositions containing emodin and related hydroxyanthraquinones may be administered topically as ophthalmic compositions, nasal sprays, and certain vaginal and rectal suppositories, or systemically as intravenous compositions, capsules, tablets, syrups, and other liquids.

It is, therefore, an object of the present invention to provide active therapeutic substances having antiviral activity against HCMV and methods of administering said compositions.

Another important object of the present invention is to provide non-nucleoside antiviral compositions and methods of administering said compositions which specifically attack HCMV without substantially inhibiting normal cellular metabolism.

Additional objects and advantages of the present invention will be apparent from the following description and appended claims taken in conjunction with the accompanying drawings or may be learned by the practice of the invention.

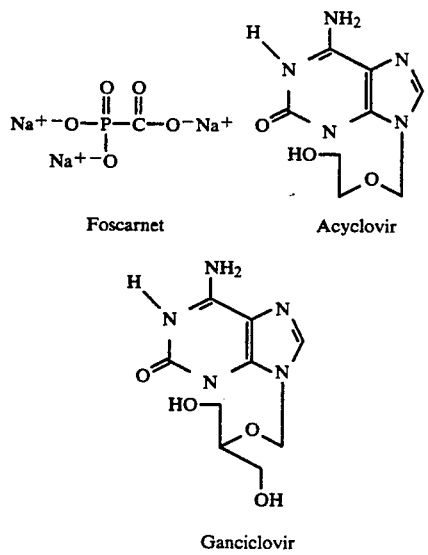

Foscarnet  Acyclovir

Ganciclovir

Figure 2:
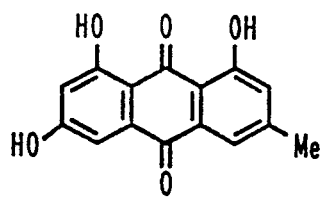
Figure 2:
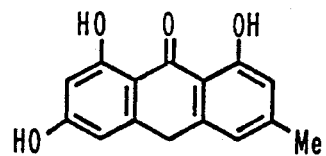
Figure 2:
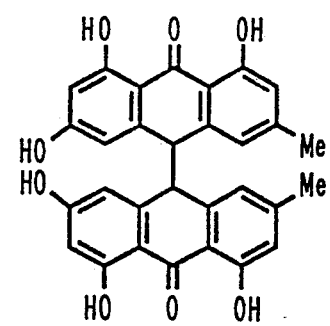
Figure 2:
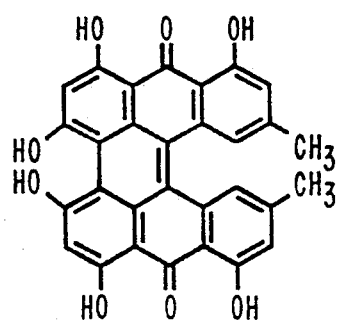
Figure 2:
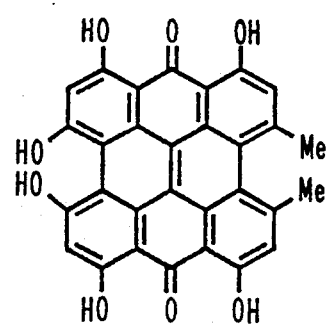
Figure 2:
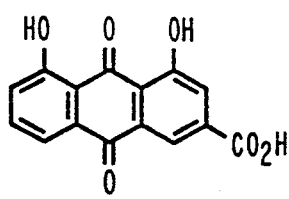
Figure 2:
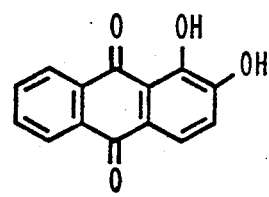
Figure 2:
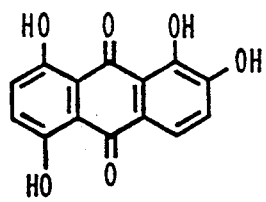
Figure 2:
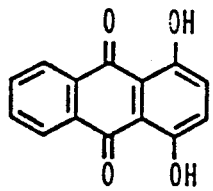
Figure 2:
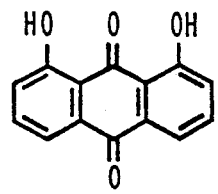

FIG. 2 contains a representation of the structural formula for various anthraquinone derivatives which were active against HCMV.

Figure 3:
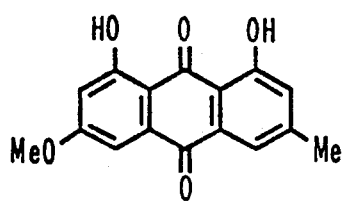
Figure 3:
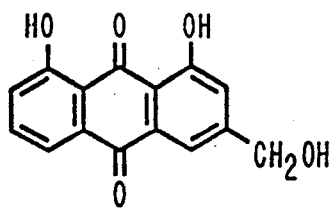
Figure 3:
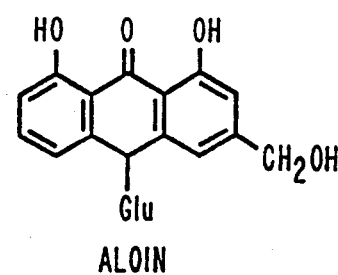
Figure 3:
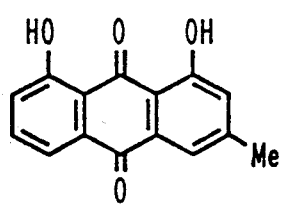
Figure 3:
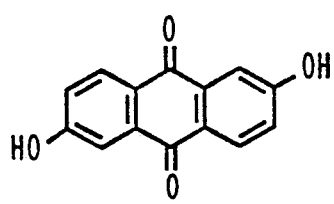
Figure 3:
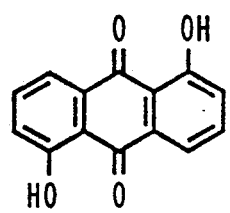
Figure 3:
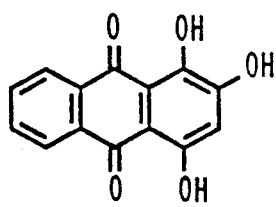
Figure 3:
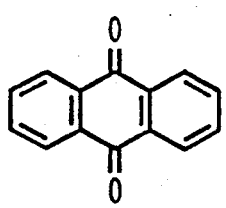
Figure 3:
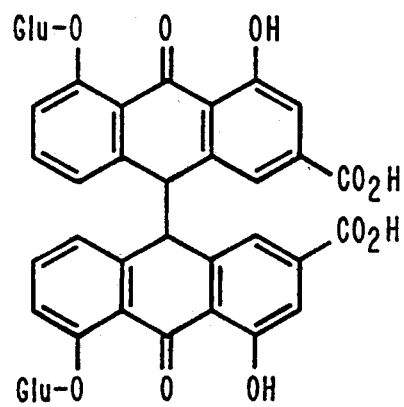

FIG. 3 contains a representation of the structural formula for various anthraquinone derivatives which were not significantly active against HCMV.

Figure 4:
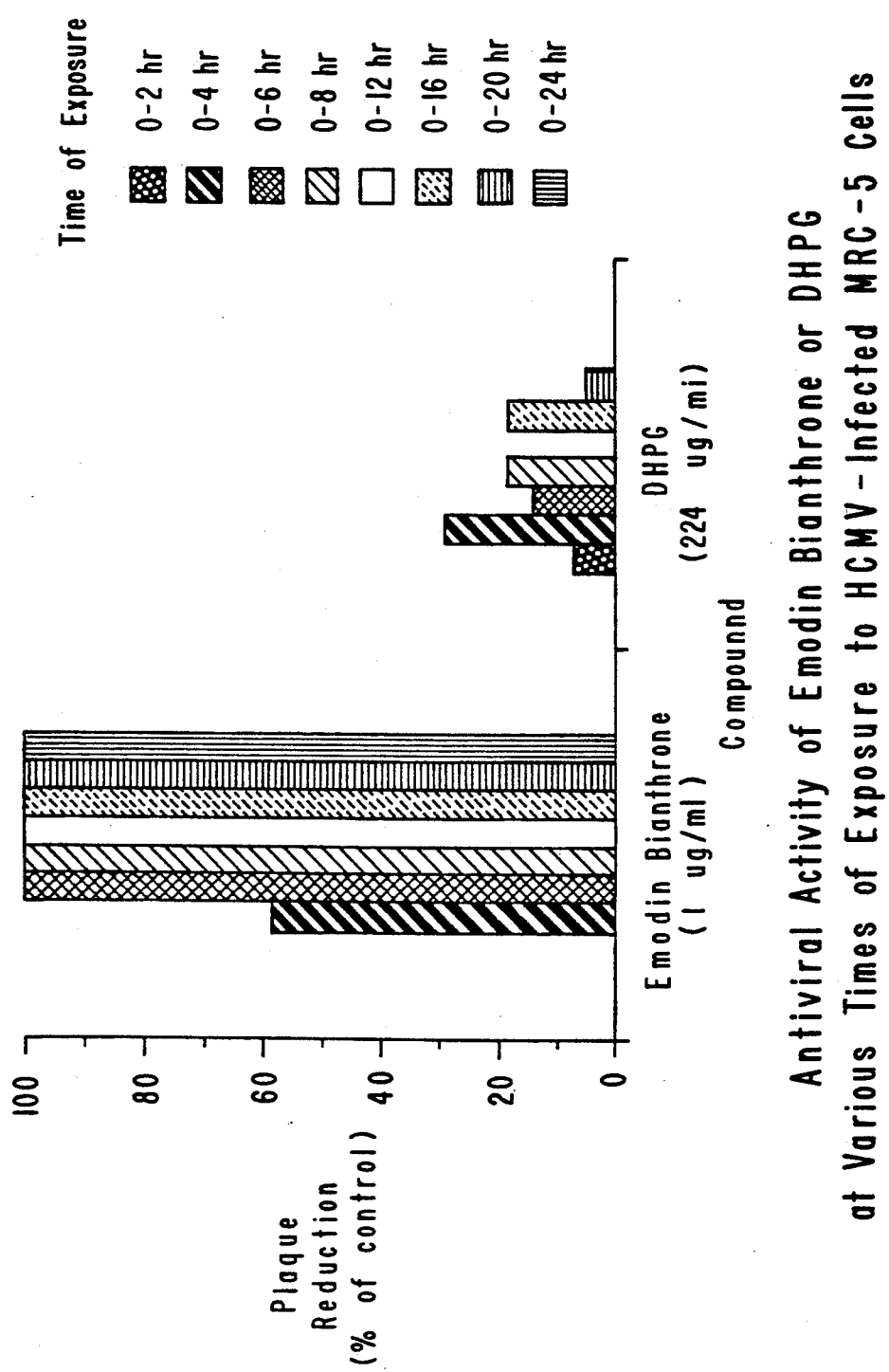

FIG. 4 is a graphical representation of the results of Example 9 comparing the antiviral activity of emodin bianthrone and DHPG at various exposure times to human cytomegalovirus.

DETAILED DESCRIPTION OF THE PREFERRED EMBODIMENTS

In recent years there has been growing interest in identifying safe and effective antiviral compounds. Much of the scientific effort has been to identify and synthesize nucleosides and nucleoside analogs which interfere with virus replication. Nucleosides, however, can be very toxic.

In an effort to uncover new non-nucleoside compounds possessing antiviral activity, effort has been given to identify safe naturally occurring compounds and derivatives thereof. As will be discussed in greater detail hereinafter, it has been found that emodin and certain related hydroxyanthraquinone derivatives and salts possess significant antiviral activity against human cytomegalovirus ("HCMV").

Emodin and certain related hydroxyanthraquinone derivatives which are the subject of this application are known compositions. Emodin, for example, as identified in the *Merck Index*, Tenth Edition, 1983, is naturally occurring and can be found in rhubarb root, alder buckthorn (*Rhamnus frangula* L.), and other plants. The hydroxyanthraquinones and their glycosides are the active principles in these preparations and act directly on the lower bowel. This class of compounds is also found in certain fungi.

Figure 1:
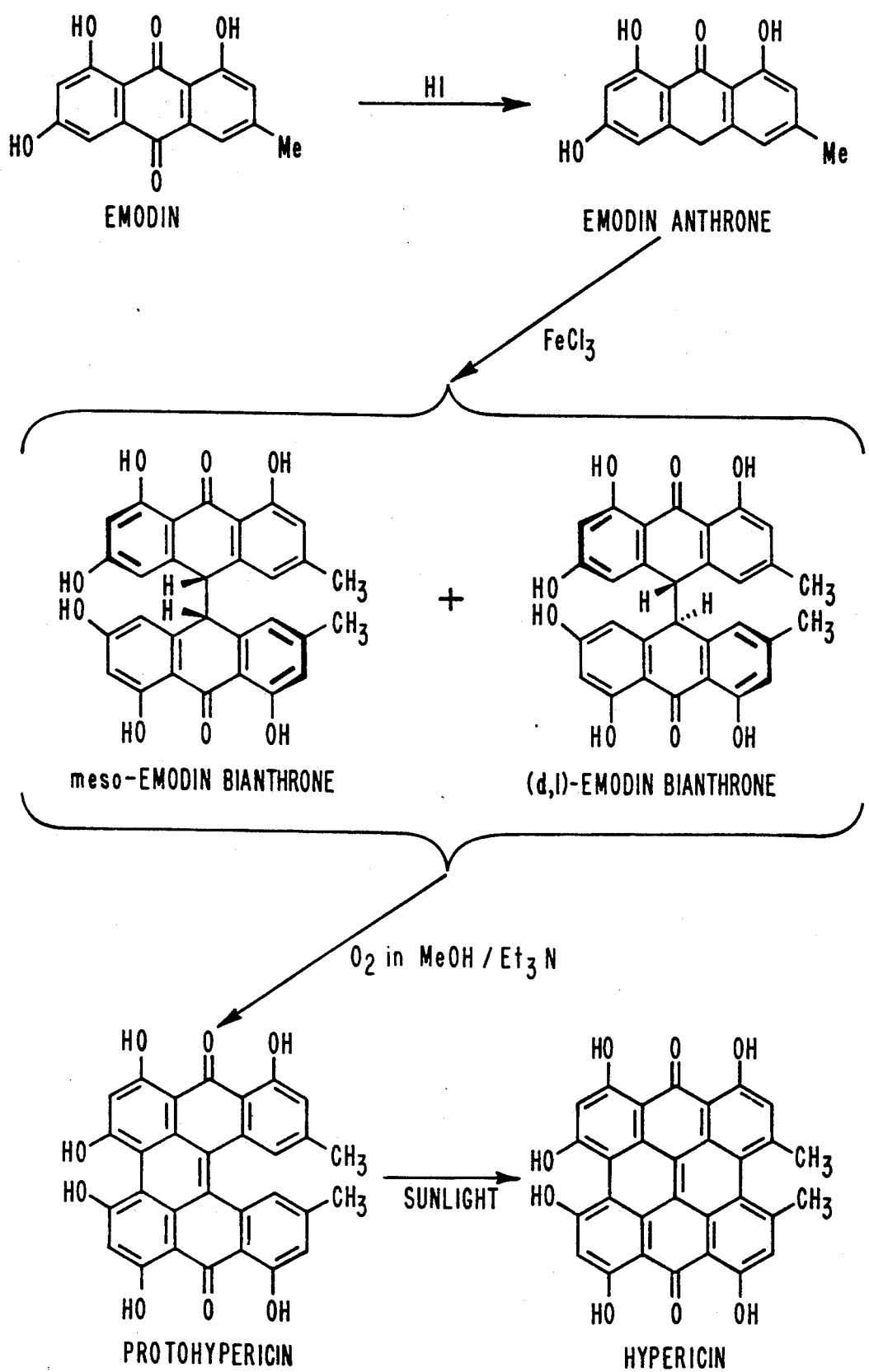
FIG. 1 is a schematic representation of the chemical reaction outlining the formation of emodinanthrone, emodin bianthrone, protohypericin, and hypericin from emodin.

Emodin anthrone, emodin bianthrone, protohypericin, and hypericin may be synthesized from emodin according to the procedure identified in FIG. 1. Emodin anthrone is formed by reducing emodin with hydroiodic acid (HI) in glacial acetic acid, as described in Jacobson, R. A. and Adams, R., *J. Amer. Chem. Soc.*, vol. 46, pp. 1312-16 (1924), which is incorporated herein by specific reference.

Emodin anthrone is dimerized to give the 10,10'-coupled bianthrones by reacting emodin anthrone with ferric chloride (FeCl₃) in ethanol, as described in Kinget, R., *Planta. Med.*, vol. 15, pp. 233-39 (1967), which is also incorporated herein by specific reference. This reaction results in two diastereomers, the meso and the dl-pair. These compounds are readily separated on reverse phase high pressure liquid chromatography ("HPLC"). Subsequent oxidation of the bianthrones with oxygen in methanol containing triethylamine produces protohypericin, which is converted into hypericin upon exposure to sunlight. Alternatively air oxidation of the bianthrones in hot ammonium hydroxide and exposure to sunlight give rise to hypericin. The resulting compounds are characterized by HPLC, thin layer chromatography ("TLC"), and ultraviolet/visual spectrometry.

Initial screening of hypericin, protohypericin, emodin anthrone, and emodin bianthrones against HCMV in vitro demonstrate that hypericin, protohypericin, and the emodin bianthrones are active, but the emodin anthrone is not active. In addition, the compounds quinalizarin, rhein, alizarin, physcione, aloin, anthraquinone, chrysophanol, aloe-emodin, 1,8-dihydroxyanthraquinone, quinizarin, anthraflavic acid, purpurin, anthrarufin, and sennosides A & B have also been tested against HCMV. The chemical structures of these compounds are illustrated in FIG. 2. Emodin, emodin anthrone (active against DHPG resistant HCMV strain), emodin bianthrone (mixed, d,l, and meso), protohypericin, hypericin, rhein, alizarin, quinalizarin, quinizarin, and 1,8-dihydroxyanthraquinone show activity against HCMV.

Based on the compounds tested, it is possible to characterize the structure activity relationships in this class of compounds. A 1,3-dihydroxy substitution pattern in the same ring seems to correlate with biological activity, with the exception of rhein, alizarin, quinalizarin, and the less active compounds 1,8-dihydroxyanthraquinone and quinizarin. Although rhein does not have a 3-hydroxyl group, it does have an acidic hydrogen on the carboxyl group in the comparable position. The 1,2-dihydroxyanthraquinones are active (quinalizarin and alizarin), but more than two hydroxyls in one ring seems to block activity as in the case of purpurin. Both 1,8-dihydroxyanthraquinone and quinizarin (1,4-dihydroxyanthraquinone) show activity but at lower levels than the other compounds.

The following is a generalized structure for antiviral compounds within the scope of the present invention:

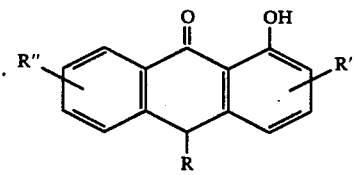

Wherein R is 2H or =O; R' is OH, H, or COOH (single substitution); and R" is OH, H, and/or alkyl (single or multiple substitution).

Hypericin, protohypericin, and emodin bianthrone are dimeric structures of emodin. All of these three compounds exhibit good biological activity. As a result, it would be reasonable to assume that such like dimeric structures of other active hydroxyanthraquinones would also be active.

The following are generalized dimer structures for antiviral compounds within the scope of the present invention:

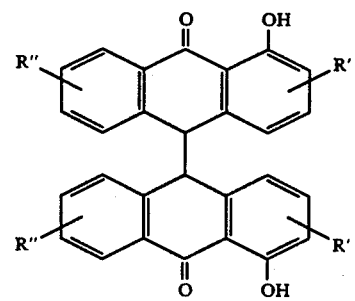

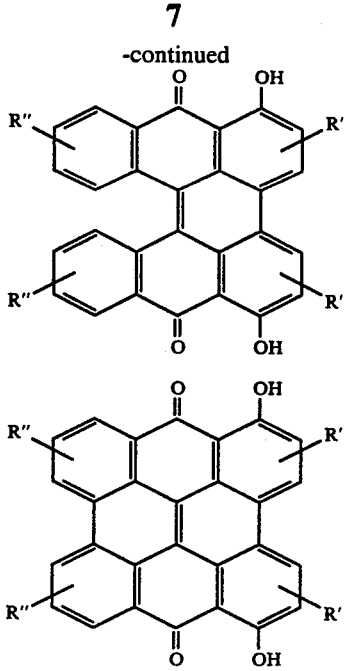

Wherein R is 2H or =O; R' is OH, H, or COOH (single substitution); and R" is OH, H, and/or alkyl (single or multiple substitution).

Pharmaceutical compositions within the scope of the present invention may be administered intravenously. Such compositions are advantageously administered "piggyback" with generally accepted intravenous fluids. It is currently anticipated that a typical induction treatment would include from about 2 milligrams/kg/day to about 10 milligrams/kg/day of the active ingredient (administered over a constant rate for one hour twice a day) for 2 to 3 weeks.

A typical maintenance treatment would include from about 1 milligram/kg/day to about 5 milligrams/kg/day of the active ingredient (administered over a constant rate for one hour once a day), increasing to double the dosage if symptoms reoccur. Of course, it will be appreciated that there are many factors which affect the actual dosage needed under the circumstances such as the state of the disease, the pharmacological activity of the active ingredient, and the patient's individual susceptibility to the active ingredient.

As used herein, the active ingredient preferably includes emodin, emodin anthrone, emodin bianthrones, protohypericin, hypericin, rhein, alizarin, quinalizarin, quinizarin, and 1,8-dihydroxyanthraquinone, related hydroxyanthraquinones, hydroxyanthrones, or dimers thereof, or mixtures thereof including salts and other pharmacologically active forms thereof, which have been shown to possess anti-HCMV activity.

The pharmaceutical compositions within the scope of the present invention may also be administered systemically in oral solid dosage forms, ophthalmic, suppository, aerosol, or other similar dosage forms. In addition to the active ingredient, such pharmaceutical compositions may contain pharmaceutically acceptable carriers and other ingredients known to enhance and facilitate drug administration.

For oral administration, such compositions are advantageously formed into oral tablets or capsules. The active ingredient may also be incorporated into a liquid or syrup form in an alcohol or glycerin base. The initial oral dosage of active antiviral compounds is preferably in the range from about 10 mg/kg/day to about 100 mg/kg/day in three divided doses for approximately 10 days. Thereafter, a maintenance dosage of from about 1 mg/kg/day to about 50 mg/kg/day in three divided doses is preferably administered to the patient.

Tablet or capsules are preferably formulated with suitable binders and pharmacologically acceptable carriers such as starch, gelatin, sugars, natural and synthetic gums, carboxymethylcellulose, polyvinylpyrrolidone, Veegum, waxes, and ethyl cellulose; disintegrants such as starches, clays, celluloses, algins, gums, crosslinked polymers, and bentonite; lubricants such as talc, magnesium stearate, calcium stearate, and stearic acid; diluents such as microcrystalline cellulose (Avicel); and colorants such as United States approved FD&C dyes.

Typical tablets may be film coated, sugar coated, microencapsulated or impression coated and may possibly be controlled release or enteric coated. Tablets or capsules containing active antiviral compounds within the scope of the present invention may be administered orally, sublingually, or transmucosally in the vagina or buccal pouch.

The following is a typical tablet formulation prepared by the wet granulation method:

| Ingredients | Per Tablet |
| --- | --- |
| Active antiviral compound | 0.3 to 33 mg |
| Polyvinylpyrrolidone | 22.5 mg |
| Lactose | 61.8 mg |
| Alcohol 3A-200 proof | 4.5 ml |
| Stearic acid | 9 mg |
| Talc | 13.5 mg |
| Corn starch | 43.2 mg |

See *Remington's Pharmaceutical Sciences*, A. R. Gennaro, ed., Mack Publishing Co., Easton, Pa., p. 1621 (1985).

The following is a typical tablet formulation prepared by the direct compression method:

| Ingredients | Per Tablet |
| --- | --- |
| Active antiviral compound | 0.3 to 33 mg |
| Microcrystalline cellulose | 159 mg |
| Stearic acid | 9 mg |
| Colloidal silica | 2 mg |

See *Remington's Pharmaceutical Sciences*, p. 1622.

Pharmaceutical compositions of the present invention may comprise ophthalmic dosage forms such as ointments or suspensions. A typical ophthalmic ointment within the scope of the present invention preferably includes from about 3% to about 5% active antiviral compound in a petrolatum base. Petrolatum bases known in the art may be used such as a 60:40 mixture of solid and liquid petrolatum. A petrolatum base allows for longer drug contact time and generally greater drug bioavailability. The petrolatum base is also nonirritating to the eye and provides good stability and storage. Mineral oil trolatum, anhydrous lanolin, or a polyethylene/mineral oil gel are possible substitutes for the petrolatum base.

A preservative, such as 0.004% benzalkonium chloride is also preferably included in the ophthalmic ointment. Other possible ophthalmic preservatives which may be used include chlorobutanol, parahydroxy benzoates, aromatic alcohols, organic mercurials, and quaternary ammonium compounds.

A typical ophthalmic suspension preferably includes from about 1% to about 3% active antiviral compound in an aqueous solution. Suitable aqueous solutions used in the art as ophthalmic suspensions may be used. One typical solution includes the antiviral compound in sodium phosphate (a buffer), sodium chloride, and 0.002% thimerosal as a preservative. The buffer maintains the pH of the suspension within the range from about 7.2 to about 7.6, and optimally at a pH of about 7.4 which is the pH of the tear fluid.

Drops of either an ophthalmic ointment or suspension are typically used every two hours. Ophthalmic ointments are particularly useful in treating retinitis. However, in more progressive stages of the disease both ophthalmic ointment and oral dosage forms would likely be used.

The pharmaceutical compositions within the scope of the present invention may also be advantageously formed into suppositories for rectal and vaginal administration. Rectal compositions preferably include from about 1 mg to about 50 mg of active antiviral compound in a 2 gram dose. In addition to the active ingredient, rectal compositions include a suppository base such as natural or synthetic triglycerides, gelatins, and other known suppository bases known in the art.

A typical rectal suppository might include from about 0.1% to about 5% of the active antiviral compound in a base of approximately 75% polyethylene glycol of 1,000 molecular weight and 25% polyethylene glycol of 4,000 molecular weight. This suppository base has shown good heat stability. Another possible suppository base may be prepared from approximately 96% polyethylene glycol of 1,000 molecular weight and 4% polyethylene glycol of 4,000 molecular weight.

Other suppository bases known in the art, such as cocoa butter, glycerinated gelatin, hydrogenated vegetable oils, mixtures of polyethylene glycols of various molecular weights, and fatty acids esters of polyethylene glycol may also be used within the scope of the present invention.

Vaginal compositions preferably include from about 50 mg to about 250 mg of active antiviral compound in a 5 gram dose. In addition to the active ingredient, vaginal compositions include a suppository base such as those known in the art. A typical vaginal suppository might include from about 1% to about 5% of the active antiviral compound in a glycerinated gelatin base with 0.025% methylparaben and 0.015% propylparaben as preservatives. Other preservatives known in the art may also be used.

For aerosol administration of the pharmaceutical compositions within the scope of the present invention, from about 50 mg to about 200 mg of the active antiviral compound is administered per delivery. Suitable aerosol dosage forms include both solutions and suspensions. Aerosol dosage forms may be used to provide local activity in the nasal areas, throat, and lungs, such as in the treatment of pneumonitis. Rapid systemic activity may be obtained when the aerosol dosage form is absorbed from the lungs directly into the bloodstream, thereby bypassing the digestive system.

A typical aerosol solution includes the following ingredients:
(1) Active antiviral compound, solubilized in ethanol with or without a surfactant (such as Tween);
(2) Preservatives, such as cetylpyridinium chloride;
(3) Antioxidants, such as ascorbic acid;
(4) Solvent blend, such as water, ethanol, glycols; and
(5) Propellants, such as $CCl_2F_2/CCl_3F$, $CCl_2F_2/C_2Cl_2F_4$, or $CCl_2F_2$ alone.

A typical aerosol suspension includes the following ingredients:
(1) Active antiviral compound, micronized and suspended;
(2) Dispersing agents, such as sorbitan oleate, oleyl alcohol, etc.;
(3) Density modifiers;
(4) Bulking agents; and
(5) Propellants, such as $CCl_2F_2/CCl_3F$, $CCl_2F_2/C_2Cl_2F_4$, or $CCl_2F_2$ alone.

Aerosolization for both solution and suspensions may be achieved using a variety of self-pressurized packages.

Other possible dosage forms, such as nanoparticles, liposomes, resealed erythrocytes, and immunologically based systems may also be used to administer the active ingredients within the scope of the present invention.

Nanoparticles are one of several types of systems known collectively as colloidal drug delivery systems. Microcapsules, nanocapsules, macromolecular complexes, polymeric beads, microspheres, and liposomes are considered nanoparticles. A nanoparticle is a particle containing a dispersed drug with a diameter of 200-500 nm. The size of the nanoparticle allows it to be administered intravenously via injection.

When phospholipids are dispersed in aqueous media, multilamellar concentric bilayer vesicles are formed with aqueous media separating the lipid bilayers. These systems are commonly referred to as multilamellar liposomes or vesicles and have diameters from 25 nm to 4 $\mu$m. Sonication of multilamellar liposomes results in the formation of small unilamellar vesicles with diameters in the range of 200-500 Å, containing aqueous solution in the core. The liposome acts as the carrier of the active therapeutic agent.

When erythrocytes are suspended in a hypotonic medium, they swell to about one and a half times their normal size, and the membrane ruptures resulting in the formation of pores with diameters from about 200 Å to about 500 Å. The pores allow equilibration of the intracellular and extracellular solutions. If the ionic strength of the media is then adjusted to isotonicity and the cells are incubated at 37° C., the pores will close and cause the erythrocyte to "reseal." Using this technique with a drug present in the extracellular solution, it is possible to entrap up to 40% of the drug inside the resealed erythrocyte and to use the resealed erythrocytes as drug carriers.

The formation of a dissociable complex of a drug with a macromolecular is a viable method of achieving a sustained-release effect. If the macromolecule used is an antibody, an antigen-specific targeted effect can also be achieved.

EXAMPLES

The following examples illustrate the antiviral activity of emodin, emodin anthrone, emodin dimers, and related hydroxyanthraquinone derivatives within the scope of the present invention. These examples are intended to be purely exemplary of the use of the invention and should not be viewed as limiting the scope of the present invention.

EXAMPLE 1

In this example, in vitro antiviral tests of emodin, an emodin dimer (hypericin), and ganciclovir ("DHPG") against human cytomegalovirus (HCMV) were performed. The DHPG, known to possess antiviral activity against HCMV, was obtained from Syntex Laboratories, Inc., Palo Also, Cal. The human cytomegalovirus was strain AD169 originally provided by the American Type Culture Collection ("ATCC"), Rockville, Md. Human diploid embryonic lung cells (MRC-5) were also obtained from the ATCC.

One milliliter of tissue culture grade dimethyl sulfoxide ("DMSO") (ATCC lot #150341) was added to 1 mg amounts of hypericin and emodin. Each compound seemed to dissolve completely. The resulting solutions were clear, with hypericin having a blood red color and emodin a bright yellow color. These preparations were stored at $-18°$ C.

The preparations were thawed and diluted 1:100 in tissue culture medium (DMEM, 2% fetal bovine serum ("FBS"), 0.1% NaHCO$_3$, 50 μg gentamicin/ml) with 0.01% Tween 80 added, to prepare the 10 μg/ml concentrations used. Further 0.5 log$_{10}$ dilutions were made in the same type medium. The DHPG was dissolved and diluted in tissue culture medium lacking Tween 80.

The virus was diluted in tissue culture medium without Tween 80. Growth medium was decanted from established monolayers of MRC-5 cells in 24-well tissue culture plates. One ml of diluted virus was placed in all wells except cell control wells, in which 1.0 ml of sterile virus diluent was placed. The plates were centrifuged at 2200 rpm for 30 minutes at room temperature to allow the virus to adsorb. The medium was aspirated from each well and 0.8 ml of the proper drug dilution was placed in test wells (2 wells/dilution). Tissue culture medium with 0.01% Tween 80 (0.8 ml/well) was added to 4 cell control and 8 virus control wells.

The plates were incubated at 37° C. in a moist atmosphere of 5% CO$_2$, 95% air until virus plaques could be distinguished in the virus control wells. The medium was then aspirated from all wells and the cells were stained by adding 0.3 ml of 0.2% crystal violet in 10% buffered formalin to each well. After 15 minutes, the stain was aspirated, the plates were rinsed in running tap water until the water was clear, and the plates were inverted and dried at room temperature. Plaques were counted by use of a dissecting microscope.

The experimental results, summarized in Table 1, confirm the anti-HCMV activity of hypericin and emodin.

TABLE 1

Antiviral Tests (Plaque Reduction) of Emodin and Hypericin versus the Human Cytomegalovirus, Strain AD-169 in MRC-5 Cells.

| Compound Concentration (μg/ml) | Emodin Number of Plaques[a] | Emodin % Inhibition | Hypericin Number of Plaques[a] | Hypericin % Inhibition | DHPG Number of Plaques[a] | DHPG % Inhibition |
|---|---|---|---|---|---|---|
| 500 | | | | | 0 | 100 |
| 250 | | | | | 0 | 100 |
| 10 | 0 | 100 | 0 | 100 | | |
| 3.2 | 0 | 100 | 6 | 92 | | |
| 1.0 | 22 | 72 | 53 | 33 | | |
| 0.32 | 78 | 1 | 53 | 33 | | |
| 0.1 | 72 | 9 | 72 | 9 | | |
| 0.032 | 79 | 0 | 72 | 9 | | |
| 0 | | | 79 | | | |
| ED$_{50}$: | | | 0.8 μg/ml | | 0.9 μg/ml | |
| CD$_{50}$: | | | ≈10 μg/ml | | ≈10 μg/ml | |
| TI: | | | ≈12 | | ≈11 | |

[a]Average of two wells, except virus controls which are an average of 7 wells.

EXAMPLE 2

In this example, in vitro antiviral tests of emodin, emodin anthrone, emodin bianthrone (mixed, meso, and dl), hypericin, protohypericin, meso sennoside B, (+) sennoside A, anthraflavic acid, chrysophanol, and aloe emodin against human cytomegalovirus (HCMV) were performed. The human cytomegalovirus was strain AD-169 and was originally provided by the American Type Culture Collection (ATCC), Rockville, Md. Human diploid embryonic lung cells (MRC-5) were also obtained from the ATCC.

The compounds were dissolved in absolute ethanol containing 0.1% Tween 80. Unused portions of these solutions were stored at $-18°$ C. and thawed immediately prior to each repeated usage. The ethanol solutions were diluted 1:100 in cell culture medium (DMEM, 2% fetal bovine serum ("FBS"), 0.1% NaHCO$_3$, 50 μg gentamicin/ml) without Tween 80 added, and then diluted 1:4 in the same cell culture medium with 0.001% Tween 80 added, to prepare the 10 μg/ml concentrations used. Further 0.5 log$_{10}$ dilutions were made in the same cell culture medium with 0.001% Tween 80. The virus was diluted in tissue culture medium without Tween 80.

Growth medium was decanted from established monolayers of MRC-5 cells in 24-well tissue culture plates. One ml of diluted virus was placed in all wells except cell control wells, in which 1.0 ml of sterile virus diluent was placed. The plates were centrifuged at 2200 rpm for 30 minutes at room temperature to allow the virus to absorb. The medium was aspirated from each well and 0.8 ml of the proper drug dilution was placed in test wells (2 wells/dilution).

Tissue culture medium with 0.001% Tween 80 (0.8 ml/well) was added to cell control and virus control wells. The plates were incubated at 37° C. in a moist atmosphere of 5% CO$_2$, 5% air until virus plaques could be distinguished in the virus control wells. The medium was then aspirated from all wells and the cells were stained by adding 0.3 ml of 0.2% crystal violet in 10% buffered formalin to each well. After 15 minutes, the stain was aspirated, the plates were rinsed in running tap water until the water was clear, and the plates were inverted and dried at room temperature. Plaques were counted by use of a dissecting microscope.

The results of Example 2 are shown in Table 2. It should be noted that the compounds tested in Example 2 were prepared in ethanol rather than DMSO as in Example 1, except for protohypericin. The toxicity seen in the results of Example 2 was more pronounced than in Example 1. It is currently not known whether this additional toxicity is due to differences in preparation of the compounds, age of the cells when used, or amount of time the compounds were on the cells prior to plaques being counted.

and is resistant to DHPG. DHPG (ganciclovir) is known to be active against normal HCMV. Human diploid embryonic lung cells (MRC-5) were also obtained from the ATCC. The procedure of Example 2 was followed except that the DHPG-resistant virus was used. The results of Example 3 are shown in Table 3.

TABLE 3

Antiviral Test (Plaque Reduction) of Emodin, Emodin Anthrone, Emodin Bianthrone, Hypericin, Rhein, Alizarin, Quinalizarin, and DHPG versus HCMV, Strain C8805-37, in MRC-5 Cells.

| Compound Concentration ($\mu$g/ml) | Emodin | Emodin Anthrone | Emodin Bianthrone | Hypericin | Rhein | Alizarin | Quinalizarin | DHPG |
|---|---|---|---|---|---|---|---|---|
| 10.0 | Toxic | Toxic | Toxic | 98 | 100 | 97 | 98 | 51 |
| 3.2 | 100 | 100 | 100 | 93 | 100 | 75 | 88 | 26 |
| 1.0 | 46 | 24 | 90 | 52 | 49 | 21 | 42 | 21 |
| 0.32 | 0 | 0 | 38 | 18 | 0 | 0 | 0 | 0 |
| 0.1 | 0 | 0 | 23 | 0 | 38 | 0 | 20 | N.D.[a] |
| 0.032 | 0 | 0 | 33 | 0 | 0 | 19 | 44 | N.D. |
| 0.01 | 0 | 0 | 0 | 0 | 0 | 0 | 21 | N.D. |
| ED50 ($\mu$g/ml): | 1.0 | 1.2 | 0.4 | 0.9 | 0.5 | 0.9 | 0.4 | 48.8 |
| CD50 ($\mu$g/ml): | 3.4 | 2.6 | 1.8 | ~10 | >10 | >10 | >10 | >1000 |
| TI: | 3.4 | 2.2 | 4.5 | ~11 | >20 | >11 | >25 | >20 |

[a]Not Done.

In a comparison of the results of Example 2 with those of Example 3, it appears that the time of exposure to the cells could be very important, due to the reduction of toxicity seen for all compounds except emodin in

TABLE 2

Antiviral Tests (Plaque Reduction) of Anthraquinone Derivatives versus HCMV, Strain AD-169 in MRC-5 Cells

| Compound Concentration ($\mu$g/ml) | Percent Inhibition of Plaque Numbers (Compared to Virus Controls) | | | | | | |
|---|---|---|---|---|---|---|---|
| | Emodin | Emodin Anthrone | Emodin Bianthrone (mixed) | Emodin Bianthrone (d,l) | Emodin Bianthrone (meso) | Hypericin | Protohypericin |
| 10 | toxic | toxic | toxic | toxic | toxic | toxic | 97 |
| 3.2 | 100 | toxic | toxic | toxic | toxic | toxic | 63 |
| 1.0 | 39 | 0 | 100 | 33 | 32 | 63 | 0 |
| 0.32 | 0 | 0 | 0 | 0 | 0 | 0 | 0 |
| 0.1 | 0 | 0 | 0 | 0 | 0 | 0 | 0 |
| 0.032 | 0 | 0 | 0 | 0 | 0 | 0 | 0 |
| 0.01 | 0 | 0 | 0 | 0 | 0 | 0 | 30 |
| ED$_{50}$ ($\mu$g/ml): | 1.1 | N.A.[b] | 0.6 | ~1.8 | ~1.9 | 0.8 | 2.9[c] |
| CD$_{50}$ ($\mu$g/ml): | 2.6 | 1.8 | 1.1 | 1.2 | 1.8 | 1.2 | 5.6 |
| TI: | 2.4 | N.A. | 1.8 | <1.0 | <1.0 | 1.5 | 2 |

| Compound Concentration ($\mu$g/ml) | Percent Inhibition of Plaque Numbers (Compared to Virus Controls) | | | | |
|---|---|---|---|---|---|
| | Meso Sennoside B | Anthraflavic Acid | Chrysophanol | Aloe-Emodin | (+) Sennoside A |
| 10 | 0 | toxic | 0 | 0 | 0 |
| 3.2 | 0 | 15 | 0 | 0 | 0 |
| 1.0 | 0 | 11 | 0 | 0 | 0 |
| 0.32 | 0 | 0 | 0 | 0 | 0 |
| 0.1 | 0 | 0 | 0 | 0 | 0 |
| 0.032 | 0 | 0 | 0 | 0 | 0 |
| 0.01 | 0 | 0 | 0 | 0 | 0 |
| ED$_{50}$ ($\mu$g/ml): | <10 | N.A. | <10 | <10 | <10 |
| CD$_{50}$ ($\mu$g/ml): | <10 | 3.4 | <10 | <10 | <10 |
| TI: | ? | <1.0 | ? | ? | ? |

[a]Dissolved in DMSO.
[b]Not Active.
[c]Ignoring the 30% inhibition at 0.01 $\mu$g/ml.

EXAMPLE 3

In this example, in vitro antiviral tests of emodin, emodin anthrone, emodin bianthrone, hypericin, rhein, alizarin, quinalizarin, and DHPG against a DHPG-resistant strain of human cytomegalovirus (HCMV) were performed. The human cytomegalovirus was strain C8805-37 and was kindly provided by the Burroughs Wellcome Co. (Research Triangle Park, N.C.). This strain of virus is a recent patient isolate of HCMV cells exposed for only 4 days (Table 3) compared to that seen in cells exposed for 6 or more days (Table 2).

Such toxicity variation profoundly affects the TI values, and also affects the ED$_{50}$ values, especially when toxicity occurs at those levels previously shown to be active against the virus. Thus, comparison of the TI values shown in Table 2 with those in Table 3 are of little value, due to the great variation in toxicity seen in the same type of cells.

However, comparison of the ED$_{50}$ values seen in the two tables is quite informative. Emodin, emodin bianthrone, and hypericin retain essentially the same activity versus the resistant strain of HCMV as they have against the AD-169 strain. In addition, emodin anthrone shows activity against the C8805-37 strain. These results indicate some difference in the mechanism of action of hypericin and the emodin compounds.

EXAMPLE 4

In this example, in vitro virucidal tests of hypericin and emodin bianthrone were performed against human cytomegalovirus strain AD-169. Solutions of the test compounds were prepared according to the procedure of Example 2. The virucidal tests were performed by mixing equal volumes of virus and test compound (at a concentration 2 times that of the final concentration shown), incubating the mixture at 37° C. for one hour, and doing a plaque titration of the resulting mixtures. The plaque titration was done by diluting the mixtures by 10-fold series dilutions in cell culture medium without the test compound. These dilutions were then exposed to fresh monolayers of MRC-5 cells in 24 well plates by 30 minutes of centrifugation at room temperature. The inoculum was removed from each well and replaced with fresh cell culture medium. The plates were incubated and stained for plaque counts when plaques could be seen forming in the virus control titrations.

The virucidal experimental results are summarized in Table 4. The results indicate some differences in mechanism of activity between hypericin and emodin bianthrone. While hypericin has strong virucidal activity against HCMV, emodin bianthrone has negligible virucidal activity against HCMV at concentrations shown to have significant anti-HCMV activity.

TABLE 4

Virucidal Test of Hypericin and Emodin Bianthrone versus HCMV, Strain AD-169. One Hour Incubation at 37° C. Compounds Removed from the Cells After Virus Absorption for 30 Minutes.

| Final Compound Concentration (μg/ml) | Hypericin Virus Titer (pfu/ml) | Hypericin Virus Reduction (pfu/ml) | Emodin Bianthrone Virus Titer (pfu/ml) | Emodin Bianthrone Virus Reduction (pfu/ml) |
|---|---|---|---|---|
| 10.0 | $<10^{1.0}$ | $\geq 10^{5.18}$ | N.D.$^a$ | — |
| 3.2 | $10^{2.3}$ | $10^{3.88}$ | $10^{5.70}$ | $10^{0.48}$ |
| 1.0 | $10^{3.08}$ | $10^{3.10}$ | $10^{6.08}$ | $10^{0.10}$ |
| 0.32 | $10^{5.23}$ | $10^{0.95}$ | $10^{6.08}$ | $10^{0.10}$ |
| 0 | $10^{6.18}$ | | | |

$^a$Not Done

EXAMPLE 5

In this example, in vitro antiviral tests of anthrarufin, alizarin, anthraquinone, and rhein against human cytomegalovirus (HCMV) strain AD-169 were performed. The procedure described in Example 2 was followed. Results of the antiviral tests are summarized in Table 5.

TABLE 5

Antiviral Test (Plaque Reduction) of Anthrarufin, Alizarin, Anthraquinone, and Rhein versus HCMV, Strain AD-169, in MRC-5 Cells.

| Compound Concentration (μg/ml) | Anthrarufin Number of Plaques | Anthrarufin % Reduction | Alizarin Number of Plaques | Alizarin % Reduction | Anthraquinone Number of Plaques | Anthraquinone % Reduction | Rhein Number of Plaques | Rhein % Reduction |
|---|---|---|---|---|---|---|---|---|
| 10.0 | 93 | 0 | 2 | 96 | 55 | 0 | Toxic | Toxic |
| 3.2 | 68 | 0 | 47 | 0 | 36 | 20 | 0 | 100 |
| 1.0 | 56 | 0 | 42 | 0 | 34 | 24 | 24 | 47 |
| 0.32 | 52 | 0 | 55 | 0 | 32 | 29 | 35 | 22 |
| 0.1 | 42 | 0 | 56 | 0 | 30 | 33 | 34 | 24 |
| 0.032 | 64 | 0 | 56 | 0 | 27 | 27 | 36 | 20 |
| 0.01 | 55 | 0 | 45 | 0 | 36 | 20 | 38 | 16 |
| ED50 (μg/ml): | >10 | | 5.8 | | >3.2 | | 1.1 | |
| CD50 (μg/ml): | >10 | | >10, ~13 | | >10 | | 3.4 | |
| TI50: | ? | | ~2 | | ? | | 3.1 | |

EXAMPLE 6

In this example, in vitro antiviral tests of purpurin, aloin, physcione, 1,8-dihydroxyanthraquinone, quinalizarin, and quinizarin against human cytomegalovirus (HCMV) strain AD-169 were performed. The procedure described in Example 2 was followed. Results of the antiviral tests are summarized in Table 6.

TABLE 6

Antiviral Test (Plaque Reduction) of Purpurin, Aloin, Physcione 1,8,-Dihydroxyanthraquinone, Quinalizarin, and Quinizarin versus HCMV, Strain AD-169, in MRC-5 Cells.

| Compound Concentration (μg/ml) | Purpurin Number of Plaques | Purpurin % Reduction | Aloin Number of Plaques | Aloin % Reduction | Physcione Number of Plaques | Physcione Reduction |
|---|---|---|---|---|---|---|
| 10.0 | toxic | toxic | 24 | 0 | 31 | 0 |
| 3.2 | 24 | 0 | 26 | 0 | 25 | 0 |
| 1.0 | 18 | 0 | 20 | 0 | 18 | 0 |
| 0.32 | 17 | 0 | 20 | 0 | 18 | 0 |
| 0.1 | 23 | 0 | 20 | 0 | 19 | 0 |
| 0.032 | 16 | 0 | 20 | 0 | 14 | 0 |
| 0.01 | 20 | 0 | 16 | 0 | 17 | 0 |
| ED50 (μg/ml): | N.A. | | >10 | | >10 | |
| CD50 (μg/ml): | 5.6 | | >10 | | >10 | |
| TI50: | N.A. | | ? | | ? | |

1,8-Dihy-

TABLE 6-continued

Antiviral Test (Plaque Reduction) of Purpurin, Aloin, Physcione
1,8,-Dihydroxyanthraquinone, Quinalizarin, and Quinizarin
versus HCMV, Strain AD-169, in MRC-5 Cells.

| Compound Concentration (μg/ml) | droxyanthraquinone | | Quinalizarin | | Quinizarin | |
|---|---|---|---|---|---|---|
| | Number of Plaques | % Reduction | Number of Plaques | % Reduction | Number of Plaques | Reduction |
| 10.0 | 12 | 0 | toxic | toxic | 7 | 0 |
| 3.2 | 8 | 0 | 0 | 100 | 6 | 0 |
| 1.0 | 10 | 0 | 8 | 10 | 10 | 0 |
| 0.32 | 12 | 0 | 6 | 40 | 10 | 0 |
| 0.1 | 10 | 0 | 4 | 60 | 8 | 0 |
| 0.032 | 9 | 0 | 3 | 70 | 8 | 0 |
| 0.01 | 10 | 0 | 5 | 50 | 8 | 0 |
| ED50 (μg/ml): | >10 | | ? | | >10 | |
| CD50 (μg/ml): | >10 | | 3.4 | | >10 | |
| TI50: | ? | | ? | | ? | |

EXAMPLE 7

Due to the low number of plaques obtained in the experiment of Example 6 for the compounds 1,8-dihydroxyanthraquinone, quinalizarin, and quinizarin, in vitro antiviral tests were performed for these compounds according to the procedure of Example 6. Rhein was also tested in this example. Results of the antiviral tests are summarized in Table 7. From the data in Table 7, quinalizarin and rhein are both definitely active. Slight activity of 1,8-dihydroxyanthraquinone and quinizarin was also observed. Rhein did not repeat the strange tailing-off of activity observed in the results of Example 5.

TABLE 7

Antiviral Test (Plaque Reduction) of 1,8-Dihydroxyanthraquinone, Quinalizarin, Quinizarin, and Rhein versus HCMV, Strain AD-169, in MRC-5 Cells.

| Compound Concentration (μg/ml) | 1,8-Dihydroxyanthraquinone | | Quinalizarin | | Quinizarin | | Rhein | |
|---|---|---|---|---|---|---|---|---|
| | Number of Plaques | % Reduction | Number of Plaques | % Reduction | Number of Plaques | Number % Reduction | of Plaques | % Reduction |
| 10.0 | 30 | 0 | toxic | toxic | 22 | 31 | Toxic | Toxic |
| 3.2 | 42 | 0 | 0 | 100 | 23 | 28 | 0 | 100 |
| 1.0 | 35 | 0 | 10 | 67 | 20 | 37 | 34 | 0 |
| 0.32 | 44 | 0 | 35 | 0 | 34 | 0 | 38 | 0 |
| 0.1 | 22 | 31 | 39 | 0 | 26 | 0 | 34 | 0 |
| 0.032 | 20 | 37 | 28 | 0 | 30 | 0 | 28 | 0 |
| 0.01 | 26 | 0 | 36 | 0 | 26 | 0 | 28 | 0 |
| ED50 (μg/ml): | >10 | | 0.9 | | >10 | | 1.8 | |
| CD50 (μg/ml): | >10 | | 3.4 | | >10 | | 2.9 | |
| TI50: | ? | | 4 | | ? | | 1.6 | |

TABLE 8

Antiviral Activity Tests (Plaque Reduction) of Hypericin and DHPG versus Murine Cytomegalovirus, Strain Smith MSGV, in 3T3 Cells.

| Compound Concentration (μg/ml) | Hypericin | | DHPG | |
|---|---|---|---|---|
| | Number of Plaques | % Reduction | Number of Plaques | % Reduction |
| 100 | N.D. | — | 0 | 100 |
| 31.6 | N.D. | — | 0 | 100 |
| 10 | 0 | 100 | 1 | 96 |
| 3.2 | 15 | 0 | 6 | 72 |
| 1.0 | 19 | 0 | 13 | 42 |
| 0.32 | 22 | 0 | 16 | 0 |
| 0.1 | 19 | 0 | N.D. | — |
| 0.32 | 25 | 0 | N.D. | — |
| $ED_{50}$ (μg/ml): | 5.6 | | 1.9 | |
| $CD_{50}$ (μg/ml): | >10 | | >100 | |
| $TI_{50}$: | >2 | | >53 | |

EXAMPLE 8

In this example, in vitro antiviral tests of hypericin and ganciclovir ("DHPG") were performed according to the procedure of Example 1, except that murine cytomegalovirus strain Smith MSGV was used instead of HCMV, strain AD169 and 3T3 cells were used instead of human diploid embryonic lung cells (MRC-5). Results of the antiviral tests are summarized in Table 8. From the results shown in Table 8, it can be seen that hypericin has in vitro activity against murine cytomegalovirus, although it is less active than against human cytomegalovirus.

EXAMPLE 9

In this example, the in vitro antiviral effect of different exposure times of emodin bianthrone and DHPG to human cytomegalovirus (HCMV) strain AD-169 were studied. The procedure described in Example 2 was followed, except that the concentration of each compound was chosen to cause 100% reduction of virus plaques if the compounds were left on the cells the entire time of the experiment. The results of Example 9 are illustrated in FIG. 4.

When DHPG, at 224 μg/ml, is left on the cells for short periods of time, essentially no anti-HCMV activity is seen. Emodin bianthrone exerts its antiviral activity very early, with complete inhibition of plaques seen in as little as 6 hours of exposure to the cells. There is no effect when only 2 hours of exposure is allowed, but a 4 hour exposure causes almost 60% plaque reduction. These results indicate that the mechanism of action of emodin bianthrone is different from that of DHPG. The rapid and complete activity would indicate that the drug is either taken into the cells very rapidly and then not easily removed, or that the drug does something to the cell which is not reversed by removal of the drug.

The short treatment time required may be a way to reduce toxicity to the cells. However, no toxicity was noticed microscopically in the cells until they had been treated 6 hours. Thus, the time at which 100% plaque reduction first occurred was the same as the time at which partial cytotoxicity was first visible.

Tables 9 and 10 summarize the antiviral activity data with respect to emodin, emodin anthrone, emodin dimers, and various hydroxyanthraquinone compounds tested in the foregoing examples against human cytomegalovirus strains AD-169 and C8805-37 (a DHPG resistant strain), respectively.

TABLE 9

Summary of Antiviral Activity Against HCMV

| Compound | ED$_{50}$ μg/ml | CD$_{50}$ (μg/ml) | TI |
|---|---|---|---|
| Emodin | 1.1, 0.8 | 2.6, ≈10 | 2.4, ≈12 |
| Emodin Bianthrone (mixed) | 0.6 | 1.1 | 1.8 |
| Emodin Bianthrone (d,l) | ≈1.8 | 1.2 | <1.0 |
| Emodin Bianthrone (meso) | ≈1.9 | 1.8 | <1.0 |
| Protohypericin | 2.9 | 5.6 | 2 |
| Hypericin | | | |
| (HCMV) | 0.8, 0.9 | 1.2, ≈10 | 1.5, ≈11 |
| (MCMV) | 5.6 | >10 | >2 |
| Rhein | 1.1, 1.8 | 3.4, 2.9 | 3.1, 1.6 |
| Alizarin | 5.8 | >10 | ≈2 |
| Quinalizarin | 0.9 | 3.4 | 4 |
| Quinizarin | >10 | >10 | ?[a] |
| 1,8-Dihydroxy-anthraquinone | >10 | >10 | ? |
| Physcione | >10 | >10 | N.A.[b] |
| Aloe-Emodin | >10 | >10 | N.A. |
| Aloin | >10 | >10 | N.A. |
| Chrysophanol | >10 | >10 | N.A. |
| Emodin Anthrone | N.A. | 1.8 | N.A. |
| Anthraflavic Acid | N.A. | 3.4 | N.A. |
| Anthrarufin | >10 | >10 | N.A. |
| Purpurin | >10 | 5.6 | N.A. |
| Anthraquinone | >3.2 | >10 | N.A. |
| Sennoside A (d,l) | >10 | >10 | N.A. |
| Sennoside B (meso) | >10 | >10 | N.A. |

[a]Slight Activity.
[b]Not Active.

TABLE 10

Summary of Antiviral Activity Against DHPG Resistant HCMV

| Compound | ED$_{50}$ (μg/ml) | CD$_{50}$ (μg/ml) | TI |
|---|---|---|---|
| Emodin | 1.0 | 3.4 | 3.4 |
| Emodin Anthrone | 1.2 | 2.6 | 2.2 |
| Emodin Bianthrone | 0.4 | 1.8 | 4.5 |
| Hypericin | 0.9 | 10 | 11 |
| Rhein | 0.5 | >10 | >20 |
| Alizarin | 0.9 | >10 | >11 |
| Quinalizarin | 0.4 | >10 | >25 |
| (DHPG) | (48.8) | (>1000) | (>20) |

From the foregoing, it will be appreciated that the present invention provides active therapeutic substances having antiviral activity against HCMV and methods of administering said compositions.

Additionally, it will be appreciated that the present invention provides non-nucleoside antiviral compositions and methods of administering said compositions which specifically attack HCMV at levels which are not deleterious to the cell.

The present invention also provides antiviral compositions that exhibit antiviral activity against DHPG resistant strains of HCMV.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A method for treating a viral disease caused by human cytomegalovirus comprising:
   (a) obtaining a therapeutically effective dose of an antiviral compound which is a dimer of two compounds of the formula

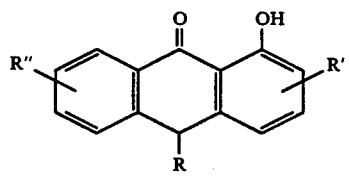

wherein R is 2H or =O; R' is OH, H, or COOH (single substitution); and R" is OH, HH, or alkyl (single or multiple substitution); and pharmaceutically acceptable salts thereof, said antiviral compound having antiviral activity in humans against a viral disease caused by human cytomegalovirus; and (b) administering the antiviral compound to a patient.

2. A method for treating a viral disease as defined in claim 1, wherein the antiviral compound is hypericin.

3. A method for treating a viral disease as defined in claim 1, wherein the antiviral compound is emodin bianthrone.

4. A method for treating a viral disease as defined in claim 3, wherein the emodin bianthrone comprises the d,l isomer.

5. A method for treating a viral disease as defined in claim 3, wherein the emodin bianthrone comprises the meso isomer.

6. A method for treating a viral disease as defined in claim 1, wherein the antiviral compound is protohypericin.

* * * * *

UNITED STATES PATENT AND TRADEMARK OFFICE
CERTIFICATE OF CORRECTION

PATENT NO. : 5,316,768
DATED : May 31, 1994
INVENTOR(S) : BRONWYN G. HUGHES et al.

It is certified that error appears in the above-indentified patent and that said Letters Patent is hereby corrected as shown below:

Column 4, line 29, after "is directed" insert --to--
Column 4, line 65, "emodinanthrone" should be --emodin anthrone--
Column 7, line 42, "reoccur" should be --recur--
Column 11, line 28, "Palo Also" should be --Palo Alto--
Columns 11 and 12, Table 1, line 12, "0.32" should be --0.032--
Columns 11 and 12, Table 1, line 14, "0.032" should be --0.32--
Columns 13 and 14, Table 2, line 28, each of the four occurrences of "<10" should be -->10--
Columns 13 and 14, Table 2, line 29, each of the four occurrences of "<10" should be -->10--
Columns 13 and 14, the order of Table 2 and Table 3 should be reversed
Column 17, line 5, Table 6, "droxyanthraquinone" should be --1,8-Dihydroxyanthraquinone--
Columns 17-18, Table 7, lines 6-8, "of Plaques" should be --Number of Plaques-- (two occurrences)
Columns 17-18, Table 7, lines 6-8, "Number % Reduction" should be --% Reduction-- (two occurrences)

Signed and Sealed this

Thirteenth Day of December, 1994

Attest:

BRUCE LEHMAN

Attesting Officer

Commissioner of Patents and Trademarks